United States Patent [19]
Medoff et al.

[11] Patent Number: 5,973,035
[45] Date of Patent: Oct. 26, 1999

[54] CELLULOSIC FIBER COMPOSITES

[75] Inventors: Marshall Medoff, Brookline; Arthur Lagace, Newtonville, both of Mass.

[73] Assignee: Xyleco, Inc., Brookline, Mass.

[21] Appl. No.: 08/961,863

[22] Filed: Oct. 31, 1997

[51] Int. Cl.[6] .................................. C08J 3/00; C08J 3/20; C08L 1/00; C08L 99/00
[52] U.S. Cl. ................................ 524/13; 524/14; 524/76; 523/129
[58] Field of Search .................................. 524/13, 14, 35, 524/72, 76; 523/129

[56] References Cited

U.S. PATENT DOCUMENTS

| | | |
|---|---|---|
| 1,824,221 | 9/1931 | Mason . |
| 2,516,847 | 8/1950 | Boehm . |
| 3,516,953 | 6/1970 | Wood . |
| 3,718,536 | 2/1973 | Downs et al. . |
| 3,943,079 | 3/1976 | Hamed . |
| 4,112,038 | 9/1978 | Garner . |
| 4,113,908 | 9/1978 | Shinomura ................. 428/113 |
| 4,204,010 | 5/1980 | Kramm et al. ............... 427/44 |
| 4,244,847 | 1/1981 | Posiviata et al. ........... 525/133 |
| 4,265,846 | 5/1981 | Shen et al. . |
| 4,279,790 | 7/1981 | Nakajima . |
| 4,559,376 | 12/1985 | Kubát . |
| 4,608,922 | 9/1986 | Pöhl . |
| 4,632,170 | 12/1986 | Pöhl . |
| 4,717,742 | 1/1988 | Beshay . |
| 4,746,688 | 5/1988 | Bistak et al. . |
| 4,791,020 | 12/1988 | Kokta ....................... 428/326 |
| 4,810,445 | 3/1989 | Lamb, Sr. et al. . |
| 4,818,604 | 4/1989 | Tock . |
| 4,874,095 | 10/1989 | Warych . |
| 4,963,603 | 10/1990 | Felegi, Jr. et al. . |
| 5,064,692 | 11/1991 | Hofmann et al. .............. 427/361 |
| 5,100,603 | 3/1992 | Neefe . |
| 5,124,519 | 6/1992 | Roy et al. . |
| 5,137,668 | 8/1992 | Lamb, Sr. . |
| 5,155,147 | 10/1992 | Dietz et al. . |
| 5,194,461 | 3/1993 | Bergquist et al. . |
| 5,254,617 | 10/1993 | Inoue et al. ................. 524/433 |
| 5,284,610 | 2/1994 | Tai . |
| 5,298,102 | 3/1994 | Pohl . |
| 5,366,790 | 11/1994 | Liebel . |
| 5,372,878 | 12/1994 | Saito ........................ 428/283 |
| 5,380,180 | 1/1995 | Lamb, Sr. . |
| 5,421,205 | 6/1995 | Pohl . |
| 5,437,766 | 8/1995 | Van Phan et al. ............. 162/127 |
| 5,439,542 | 8/1995 | Liebel . |
| 5,441,801 | 8/1995 | Deaner et al. . |
| 5,480,602 | 1/1996 | Nagaich . |
| 5,516,472 | 5/1996 | Laver ........................ 264/118 |
| 5,543,205 | 8/1996 | Liebel . |
| 5,574,094 | 11/1996 | Malucelli et al. . |
| 5,582,682 | 12/1996 | Ferretti . |
| 5,643,635 | 7/1997 | Ahn et al. ................... 427/257 |

FOREIGN PATENT DOCUMENTS

| | | |
|---|---|---|
| A-47811/90 | 1/1989 | Australia . |
| 0 161 766 A1 | 11/1985 | European Pat. Off. . |
| WO 96/13468 | 5/1996 | WIPO . |
| WO 96/13551 | 5/1996 | WIPO . |

*Primary Examiner*—Nathan M. Nutter
*Attorney, Agent, or Firm*—Fish & Richardson P.C.

[57] ABSTRACT

Composites of a resin and texturized cellulosic or lignocellulosic fiber, and methods for forming the composites, are disclosed.

16 Claims, 1 Drawing Sheet

FIGURE

CELLULOSIC FIBER COMPOSITES

BACKGROUND OF THE INVENTION

The invention relates to composites of resins and cellulosic or lignocellulosic fibers.

Resins are used in a variety of applications, for example, in food packaging. Food containers made of resins are typically used once, then discarded.

Cellulosic and lignocellulosic materials are produced, processed, and used in large quantities in a number of applications. Once used, these fibers are usually discarded as waste materials. As a result, there is an ever-increasing amount of waste cellulosic and lignocellulosic fiber, as well as waste resin.

SUMMARY OF THE INVENTION

In general, the invention features composites including a resin and texturized cellulosic or lignocellulosic fiber.

The invention features a composite including a resin, such as a thermoplastic resin, and at least about 2% by weight, more preferably at least about 5% by weight, texturized cellulosic or lignocellulosic fiber. The invention also features a composite that includes polyethylene and at least about 50% by weight texturized cellulosic or lignocellulosic fiber.

The invention further features composites, including a resin and cellulosic or lignocellulosic fiber, that have flexural strengths of at least about 3,000 psi, or tensile strengths of at least about 3,000 psi.

In addition, the invention features a process for manufacturing a composite; the process includes shearing cellulosic or lignocellulosic fiber to form texturized cellulosic or lignocellulosic fiber, then combining the texturized fiber with a resin. A preferred method includes shearing the fiber with a rotary knife cutter. The invention also features a process for manufacturing a composite that includes shearing cellulosic or lignocellulosic fiber and combining the fiber with a resin.

The term "texturized cellulosic or lignocellulosic fiber" as used herein, means that the fiber has been sheared to the extent that the internal fibers are substantially exposed. At least about 50%, more preferably at least about 70%, of these fibers have a length/diameter (L/D) ratio of at least 5, more preferably at least 25, or at least 50. An example of texturized fiber is shown in FIG. 1.

The composites of the present invention are strong, lightweight, and inexpensive. The raw materials used to make the composites are readily available; for example, they may include discarded containers composed of resins, and waste cellulosic or lignocellulosic fiber.

Other features and advantages of the invention will be apparent from the description of the preferred embodiments thereof; and from the claims.

BRIEF DESCRIPTION OF THE DRAWING

FIG. 1 is a photograph of a texturized newspaper, magnified fifty times.

DESCRIPTION OF THE PREFERRED EMBODIMENTS

A preferred composite includes a resin and texturized cellulosic or lignocellulosic fiber.

The resin encapsulates the texturized cellulosic or lignocellulosic fiber and helps control the shape of the composite. The resin also transfers the external loads to the fiber and protects the fiber from environmental and structural damage. Preferred composites include about 20% to about 60%, more preferably about 30% to about 50%, by weight of the resin.

Examples of resins include polyethylene (including, e.g., low density polyethylene and high density polyethylene), polypropylene, polystyrene, polycarbonate, polybutylene, thermoplastic polyesters, polyethers, thermoplastic polyurethane, PVC, Nylon, and other resins. It is preferred that the resins have a low melt flow index. Preferred resins include polyethylene and polypropylene with melt flow indices of less than 3 g/10 min, and more preferably less than 1 g/10 min.

The resins may be purchased as virgin material, or obtained as scrap or waste materials, and are usually purchased in pelletized form. Preferably, the resins are obtained as scrap or waste resins, as these materials are less expensive. A preferred source of resin is used polyethylene milk bottles.

The texturized cellulosic or lignocellulosic fiber provides the composite with strength. The composite may include from about 30% to about 90%, more preferably from about 50% to about 70%, of the texturized cellulosic or lignocellulosic fiber by weight. Examples of cellulosic fiber include paper and paper products; examples of lignocellulosic fiber include wood, wood fibers, and wood-related materials, as well as materials derived from kenaf, grasses, rice hulls, bagasse, cotton, and jute. A preferred cellulosic fiber is newsprint. Preferred lignocellulosic fibers include jute and kenaf.

The composites also include coupling agents. The coupling agents help to bond the hydrophilic fibers to the hydrophobic resins. Examples of coupling agents include maleic anhydride modified polyethylenes, such those in the FUSABOND® (available from Dupont, Delaware) and POLYBOND® (available from Uniroyal Chemical, Connecticut) series. A preferred coupling agent is a maleic anhydride modified high density polyethylene such as FUSABOND® MB 100D.

The composites can also contain additives known to those in the art of compounding, such as plasticizers, lubricants, antioxidants, opacificers, heat stabilizers, colorants, flame retardants, biocides, impact modifiers, photostabilizers, and antistatic agents.

Preparation of Starting Materials

If scrap cellulosic or lignocellulosic fiber is used, it should be cleaned and dried. The cellulosic or lignocellulosic fiber must then be texturized before it is combined with the thermoplastic resin. The fiber can be texturized using any one of a number of mechanical means, or combinations thereof. A preferred method of texturizing includes first cutting the cellulosic or lignocellulosic fiber into ¼- to ½-inch pieces using a standard cutting apparatus. These pieces are then sheared with a rotary cutter, such as the one (available from Sprout, Waldron Companies) described in Perry's Chem. Eng. Handbook, 6th Ed., at 8–29 (1984). The texturized fiber is then passed through a 2 mm mesh screen. It can be stored in sealed bags; it should be dried at approximately 105° C. for 4–18 hours (until the moisture content is less than about 0.5%) immediately before use.

The resin may be purchased in a pelletized or granulated form and used without further purification or drying. If surface moisture is present on the pelletized or granulated resin, however, it should be dried before use.

Preparation of Composites

The composites can be prepared as follows. A standard rubber/plastic compounding 2-roll mill is heated to 325–400° C. The resin (usually in the form of pellets or granules) is added to the heated roll mill. After about 10 minutes, the coupling agent is added to the roll mill. After another five minutes, the texturized cellulosic or lignocellulosic fiber is added to the molten resin/coupling agent mixture. The texturized fiber is added over a period of about 10 minutes.

The composite is removed from the roll mill, cut into sheets and allowed to cool to room temperature. It is then compression molded into plaques using standard compression molding techniques.

Alternatively, a mixer, such as a Banbury internal mixer, is charged with the ingredients. The ingredients are mixed, while the temperature is maintained at less than about 190° C. The mixture can then be compression molded.

In another embodiment, the ingredients can be mixed in an extruder mixer, such as a MARIS (Turin) TM 85 extruder equipped with co-rotating screws. The resin and the coupling agent are introduced at the extruder feed throat; the cellulosic or lignocellulosic fiber is introduced about 1/3 of the way down the length of the extruder into the molten resin. The internal temperature of the extruder is maintained at less than about 190° C. At the output, the composite is pelletized by cold strand cutting.

Alternatively, the mixture can first be prepared in a mixer, then transferred to an extruder for the extrusion and pellet-cutting steps.

In another embodiment, the composite can be formed into fibers, using fiber-forming techniques known to those in the art.

Properties of the Composite

The resulting composites include a network of fibers, encapsulated within a resin matrix. The fibers form a lattice network, which provides the composite with strength. Since the cellulosic or lignocellulosic fiber is texturized, the amount of surface area available to bond to the resin is increased, in comparison to composites prepared with un-texturized cellulosic or lignocellulosic fiber. The resin binds to the surfaces of the exposed fibers, creating an intimate blend of the fiber network and the resin matrix. The intimate blending of the fibers and the resin matrix further strengthens the composites.

Uses

The resin/fiber composites can be used in a number of applications. The composites are strong and light weight; they can be used, for example, as wood substitutes. The resin coating renders the composites water-resistant, so they may be used in outdoor applications. For example, the composites may be used to make pallets which are stored outdoors for extended periods of time.

EXAMPLES

Composites were prepared as follows. A standard rubber/plastic compounding 2-roll mill was heated to 325–400° C. The resin (usually in the form of pellets or granules) was added to the heated roll mill. After about 10 minutes, the resin banded on the rolls (i.e., it melted and fused to the rolls). The coupling agent was then added to the roll mill. After another five minutes, the cellulosic or lignocellulosic fiber was added to the molten resin/coupling agent mixture. The cellulosic or lignocellulosic fiber was added over a period of about 10 minutes.

The composite was then removed from the roll mill, cut into sheets, and allowed to cool to room temperature. Batches of about 80 g each were compression molded into 6"×6"×1/8" plaques using standard compression molding techniques.

One composition contains the following ingredients:

| Composition No. 1 | |
| --- | --- |
| Ingredient | Amount (g) |
| High density polyethylene[1] | 160 |
| Old newspaper[2] | 240 |
| Coupling agent[3] | 8 |

[1]Marlex 16007
[2]Texturized using rotary cutter with 2 mm mesh
[3]FUSABOND ® 100D The properties of Composition No. 1 are as follows:

| | |
| --- | --- |
| Flexural strength (psi) | 9,810 (ASTM D790) |
| Flexural modulus ($10^5$ psi) | 6.27 (ASTM D790) |

A second composition contains the following ingredients:

| Composition No. 2 | |
| --- | --- |
| Ingredient | Amount (g) |
| High density polyethylene[1] | 160 |
| Old magazines[2] | 240 |
| Coupling agent[3] | 8 |

[1]Marlex 16007
[2]Texturized using rotary cutter with 2 mm mesh
[3]FUSABOND ® 100D The properties of Composition No. 2 are as follows:

| | |
| --- | --- |
| Flexural strength (psi) | 9,060 (ASTM D790) |
| Flexural modulus ($10^5$ psi) | 6.78 (ASTM D790) |

What is claimed is:

1. A composite comprising a resin and at least about 2% by weight fiber, wherein
   the resin is selected from the group consisting of polyethylene, polypropylene, polystyrene, polycarbonate, polybutylene, thermoplastic polyesters, polyethers, thermoplastic polyurethane, PVC, and Nylon;
   the fiber is cellulosic or lignocellulosic paper that has been sheared to the extent that the internal fibers are substantially exposed.

2. The composite of claim 1, comprising at least about 5% by weight texturized fiber.

3. The composite of claim 1, wherein the fiber is newsprint.

4. The composite of claim 1, wherein the resin is magazine paper.

5. The composite of claim 1, wherein the resin is bleached kraft board.

6. The composite of claim 1, wherein the resin is a thermoplastic resin.

7. The composite of claim 6, wherein the thermoplastic resin is polyethylene.

8. The composite of claim 6, wherein the thermoplastic resin is polypropylene.

9. The composite of claim 1, wherein the composite comprises about 50% to about 70% by weight resin and about 30% to about 50% by weight fiber.

10. A composite comprising polyethylene and fiber, wherein the fiber is cellulosic or lignocellulosic paper, at least about 50% by weight of said paper having been sheared to the extent that the internal fibers are substantially exposed.

11. A composite comprising a resin and fiber, wherein the composite has a flexural strength of at least 3,000 psi,
 the fiber is cellulosic or lignocellulosic paper that has been sheared to the extent that the internal fibers are substantially exposed, and
 the resin is selected from the group consisting of polyethylene, polypropylene, polystyrene, polycarbonate, polybutylene, thermoplastic polyesters, polyethers, thermoplastic polyurethane, PVC, and Nylon.

12. The composite of claim 9, wherein the composite has a flexural strength of at least 6,000 psi.

13. The composite of claim 9, wherein the composite has a flexural strength of at least 10,000 psi.

14. The composite of claim 1, wherein at least about 50% of the fibers have a length/diameter ratio of at least 5.

15. The composite of claim 1, wherein at least about 50% of the fibers have a length/diameter ratio of at least 25.

16. The composite of claim 1, wherein at least about 50% of the fibers have a length/diameter ratio of at least 50.

* * * * *